United States Patent [19]
Bales et al.

[11] Patent Number: 5,893,846
[45] Date of Patent: Apr. 13, 1999

[54] CERAMIC COATED ENDOSCOPIC SCISSOR BLADES AND A METHOD OF MAKING THE SAME

[75] Inventors: Thomas O. Bales, Coral Gables; Robert Sixto, Jr.; Michael Sean McBrayer, both of Miami, all of Fla.

[73] Assignee: Symbiosis Corp., Miami, Fla.

[21] Appl. No.: 08/647,827

[22] Filed: May 15, 1996

[51] Int. Cl.$^6$ .................................................. A61B 17/38
[52] U.S. Cl. ............................. 606/32; 606/46; 606/48
[58] Field of Search .............................. 606/32, 41, 45, 606/46, 48–52, 174, 167, 170, 205–208; 30/350, 140

[56] References Cited

U.S. PATENT DOCUMENTS

| | | | |
|---|---|---|---|
| 3,816,704 | 6/1974 | Borom et al. | 219/462 |
| 4,850,353 | 7/1989 | Stasz et al. | |
| 4,862,890 | 9/1989 | Stasz et al. | |
| 4,870,672 | 9/1989 | Lindberg | 378/129 |
| 4,958,539 | 9/1990 | Stasz et al. | 76/104.1 |
| 5,120,596 | 6/1992 | Yamada | 428/216 |
| 5,312,434 | 5/1994 | Crainich | 606/207 |
| 5,324,289 | 6/1994 | Eggers | 606/48 |
| 5,330,471 | 7/1994 | Eggers | 606/48 |
| 5,342,381 | 8/1994 | Tidemand | 606/174 |
| 5,347,887 | 9/1994 | Rosenthal et al. | 76/104.1 |
| 5,356,408 | 10/1994 | Rydell | 606/48 |
| 5,569,243 | 10/1996 | Kortenbach et al. | 606/174 |

FOREIGN PATENT DOCUMENTS 518230  12/1992  European Pat. Off. .

Primary Examiner—John P. Lacyk
Assistant Examiner—Rosiland Kearney
Attorney, Agent, or Firm—David P. Gordon; David S. Jacobson; Thomas A. Gallagher

[57] ABSTRACT

A process for providing an endoscopic scissors blade with the necessary roughness to receive a ceramic coating, without first requiring that the blade surfaces be roughened by gritblasting, includes obtaining an investment mold with an interior textured surface. The investment mold is textured by first texturing an injection mold cavity by etching, gritblasting, or electric-discharge machining the inside surface of the injection mold cavity to produce a desired roughness. A blade pattern (wax) is then formed in the injection mold with a resulting textured surface, and using the textured blade pattern, the investment mold with the textured interior cavity is generated. When metal is injected into the investment mold using a lost wax process, the resulting cast blades will have the necessary roughness for permitting a ceramic to be bonded thereto without the need for any additional roughening. Thus, the so-formed blades are coated with a ceramic material. Such scissors blades are used in an endoscopic surgical scissors instrument and are especially useful as the scissor blades of a bipolar cautery endoscopic scissors instrument.

16 Claims, 2 Drawing Sheets

CERAMIC COATED ENDOSCOPIC SCISSOR BLADES AND A METHOD OF MAKING THE SAME

This application relates to co-owned U.S. Ser. No. 08/429,596 filed Apr. 27, 1995 and entitled "Bipolar Endoscopic Surgical Scissor Blades And Instrument Incorporating the Same" and co-owned U.S. Ser. No. 08/284,793 filed Aug. 2, 1994 and entitled "Double Acting Endoscopic Scissors With Bipolar Cautery Capability" which are hereby incorporated by reference herein in their entirety.

BACKGROUND OF THE INVENTION

1. Field of the Invention

The present invention relates generally to endoscopic surgical instruments. More particularly, the invention relates to a process of manufacturing endoscopic end effectors having a combination of conductive and non-conductive materials, end effectors made by the process, and an endoscopic surgical instrument incorporating the end effectors made by the process. The invention has particular use with respect to bipolar endoscopic cautery. For purposes herein, the term "endoscopic instruments" is to be understood in its broadest sense to include laparoscopic, arthroscopic, and neurological instruments, as well as instruments which are inserted through an endoscope.

2. State of the Art

Endoscopic surgery is widely practiced throughout the world today and its acceptance is growing rapidly. In general, endoscopic/laparoscopic surgery involves one or more incisions made by trocars where trocar tubes are left in place so that endoscopic surgical tools may be inserted through the tubes. A camera, magnifying lens, or other optical instrument is often inserted through one trocar tube, while a cutter, dissector, or other surgical instrument is inserted through the same or another trocar tube for purposes of manipulating and/or cutting the internal organ. Sometimes it is desirable to have several trocar tubes in place at once in order to receive several surgical instruments. In this manner, organ or tissue may be grasped with one surgical instrument, and simultaneously may be cut with another surgical instrument; all under view of the surgeon via the optical instrument in place in the trocar tube.

Various types of endoscopic surgical instruments are known in the art. These instruments generally comprise a slender tube containing a push rod which is axially movable within the tube by means of a handle or trigger-like actuating means. An end effector is provided at the distal end of the tube and is coupled to the push rod by means of a clevis so that axial movement of the push rod is translated to rotational or pivotal movement of the end effector. End effectors may take the form of scissors, grippers, cutting jaws, forceps, and the like. Because of their very small size and the requirements of strength and/or sharpness, end effectors are difficult to manufacture and are typically formed of forged stainless steel. As such, they form an expensive portion of the endoscopic instrument.

Modern endoscopic procedures often involve the use of electrocautery, as the control of bleeding by coagulation during surgery is critical both in terms of limiting loss of blood and in permitting a clear viewing of the surgical site. As used herein, cautery, electrocautery, and coagulation are used interchangeably. Several types of electrocautery devices for use in endoscopic surgery are described in the prior art. Monopolar electrosurgical instruments employ the instrument as an electrode, with a large electrode plate beneath and in contact with the patient serving as the second electrode. High frequency voltage spikes are passed through the instrument to the electrode (i.e., end effector) of the endoscopic instrument to cause an arcing between the instrument and the proximate tissue of the patient. The current thereby generated continues through the patient to the large electrode plate beneath the patient. Monopolar cautery has the disadvantage that the current flows completely through the patient. Because control of the current path through the body is not possible, damage can occur to tissue both near and at some distance from the surgical site. In addition, it is has been observed that monopolar cautery can result in excessive tissue damage due to the arcing between the end effector and the tissue.

In order to overcome the problems associated with monopolar cautery instruments, bipolar instruments have been introduced. In bipolar electrosurgical instruments, two electrodes which are closely spaced together are utilized to contact the tissue. Typically, one end effector acts as the first electrode, and the other end effector acts as the second electrode, with the end effectors being electrically isolated from each other and each having a separate current path back through to the handle of the instrument. Thus, in a bipolar instrument, the current flow is from one end effector electrode, through the tissue to be cauterized, to the other end effector electrode.

Co-owned U.S. Pat. Ser. No. 08/429,596 describes a pair of scissor blades for a bipolar cauterizing surgical scissors which provide the smooth operation and feel of a metal on metal cutting/shearing action. The scissor blades are comprised of an electrically conductive electrode, an electrically insulating material, and a coating of titanium dioxide, chromium dioxide, or zirconium dioxide. The electrode layer is a metal blade which is typically constructed from stainless steel, while the insulating layer is an alumina ceramic which is deposited, bonded, or otherwise fixed on the metal blade, and a titanium dioxide coating is deposited, bonded, or otherwise fixed onto the ceramic and provides the cutting edge and shearing surface. The alumina and titanium dioxide are preferably deposited on a metal scissor blade by thermal spraying of powder at high temperature and standard atmospheric pressure. The titanium dioxide is lubricous and gives the scissor blades the operational feel of metal blades.

In thermal spraying, such as by a high velocity oxygen fuel (HVOF) system, micron sized powder (granules) of the ceramic is sprinkled into the combustion chamber of a rocket-type engine and is sprayed out of the chamber onto a desired substrate. An important factor determining the quality of adhesion of the coating to the substrate is the texture of the substrate surface which the granules strike. The thermal spraying process is enhanced by a roughened substrate surface which aids in the adhesion of the coating to the metal substrate. This is because the granules, in the thermal spraying process, are given thermal and kinetic energy. A smooth surface results in poor adhesion as the granules "bounce" off the surface. In fact, even those granules which adhere to the smooth surface form a poor bond, and peeling or separation of the ceramic form the metal can easily result. However, a roughened metal surface provides a mechanical means for the ceramic powder to bond to the metal substrate and results in better adhesion of the ceramic coating.

In preparation of applying ceramic coatings by the HVOF or similar plasma thermal spray process, it is common to gritblast or sandblast metal substrates to roughen the surfaces (the terms "gritblasting" and "sandblasting" being herein used interchangeably). Gritblasting provides the surfaces with the requisite roughness needed for a proper adhesion of the ceramic granules onto the substrate. However, gritblasting the blades adds an extra step to the blade coating process, is difficult to control, and, as a result, increases the manufacture time and manufacture cost for the blades.

SUMMARY OF THE INVENTION

It is therefore an object of the invention to provide a method for providing endoscopic scissor blades with the required roughness for receiving a ceramic coating.

It is another object of the invention to provide a method for the ceramic coating of scissor blades which does not require that the substrate be gritblasted beforehand.

It is a further object of the invention to provide a method for increasing the surface roughness of endoscopic scissor blades for better adhesion of surface coatings to the blades.

It is also an object of the invention to provide a method for providing rough scissor blade surfaces by providing an investment mold used in casting the endoscopic scissor blades with a textured cavity.

It is a further object of the invention to provide a ceramic coated endoscopic scissor blade manufactured by thermal spraying a ceramic coating onto a metal scissor blade substrate which was textured by providing an investment mold cavity having a textured interior.

It is still another object of the invention to provide an endoscopic surgical instrument which incorporates ceramic coated scissor blades manufactured by thermal spraying a ceramic coating onto a metal scissor blade substrate which was textured by providing a textured investment mold cavity with a textured interior.

In accord with these objects which will be discussed in detail below, the surfaces of the scissor blades are roughened in the areas which are to be ceramic coated by providing the investment molds used to cast the scissor blades with a textured cavity. It will be appreciated that when properly textured investment molds are used, the blades cast will have the necessary roughness for the plasma thermal spray process without the need for gritblasting.

According to one embodiment of the invention, a textured investment mold cavity is obtained by etching the surface of the injection mold cavity used to form the wax pattern used in the investment casting process. According to another embodiment of the invention, the injection mold cavity is textured by gritblasting. According to a third embodiment, the injection mold cavity is textured via the use of an electrical discharge machine to produce the desired roughness on the surface of the mold cavity. By texturing the injection mold cavity, the wax pattern scissor blades formed in the cavity are provided with a rough texture. In turn, when the investment mold is formed around the blade patterns, the cavity of the investment mold will be textured. Hence, when molten metal is injected into the investment mold (using a lost wax casting process), the resulting metal endoscopic scissor blades are formed with a texture and can be coated with a ceramic without the added process time and cost of gritblasting the blade beforehand.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
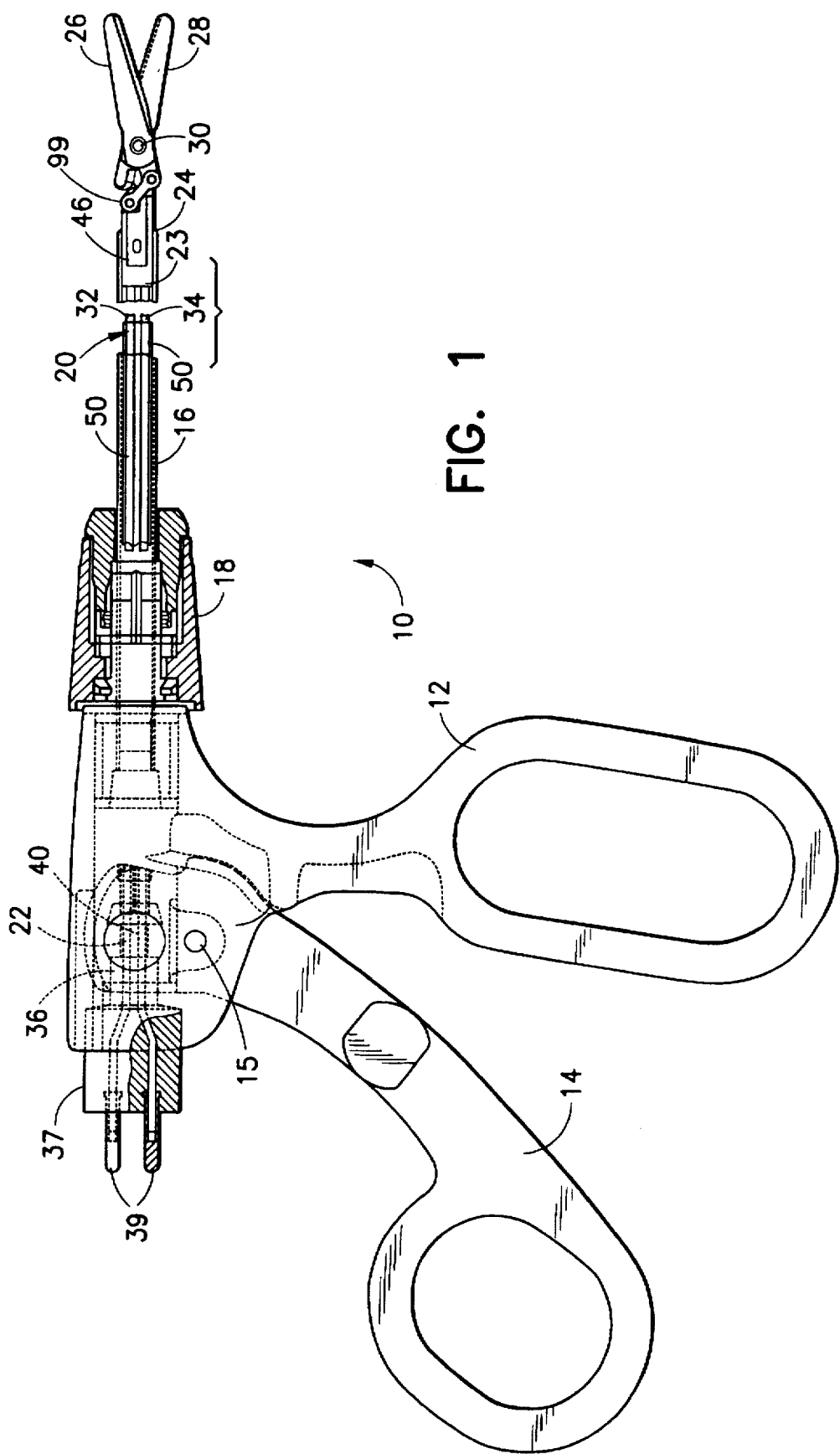
FIG. 1 is a broken side elevation view in partial section of an endoscopic bipolar scissors instrument using scissor blades made according to the invention.

Turning now to FIG. 1, an endoscopic bipolar scissors instrument 10 includes a proximal handle 12 with a manual lever actuator 14 pivotally coupled to the handle by a pivot pin 15. A hollow stainless steel tube 16 is rotatably coupled to the handle 12 and is preferably rotatable about its longitudinal axis relative to the handle 12 through the use of a ferrule 18 such as described in detail in copending application Ser. No. 08/284,793. A push rod assembly 20 extends through the hollow tube 16 and is coupled at its proximal end 22 to the manual lever actuator 14 as described in more detail in copending application Ser. No. 08/284,793. The distal end of the tube 16 has an integral clevis 24 within which a pair of scissor blades 26, 28 are mounted on an axle screw 30. The distal end 23 of the push rod assembly 20 is coupled to the scissor blades 26, 28 so that reciprocal movement of the push rod assembly 20 relative to the tube 16 opens and closes the scissor blades 26, 28. It will be appreciated that the reciprocal movement of the push rod assembly 20 relative to the tube 16 is effected by movement of the manual lever actuator 14 relative to the handle 12.

The push rod assembly 20 includes a pair of stainless steel rods 32, 34 which are molded into a proximal collar 36 and captured in a distal collar 46. The proximal collar has a radial groove 40 in its distal portion and an increased diameter proximal portion 37 which carries a pair of electrical coupling pins 39 which are electrically coupled to the rods 32, 34. As shown, the pins 39 are spaced farther apart from each other than the rods 32, 34 so as to accommodate a standard cautery connector. The rods 32, 34 are covered with insulating high density polyethylene (HDPE) tubes along substantially their entire length between the proximal and distal collars 36, 46. A plurality of spaced apart polypropylene cylinders 50 are molded about the rods between the proximal collar 36 and the distal collar 46. These cylinders stabilize the rods against helical twisting when the tube 16 is rotated and, by being discontinuous, prevent against warping of the push rod assembly. According to one embodiment, the distal collar 46 is made from two ceramic pieces which are snap fit and bonded to each other. The electrically conductive rods 32, 34 exit the distal collar 46 through opposite sides at substantially right angles. The distal ends of the rods 32, 34 are mechanically and electrically coupled to the respective blades 26, 28 by respective electrically conductive links 99.

Figure 2:
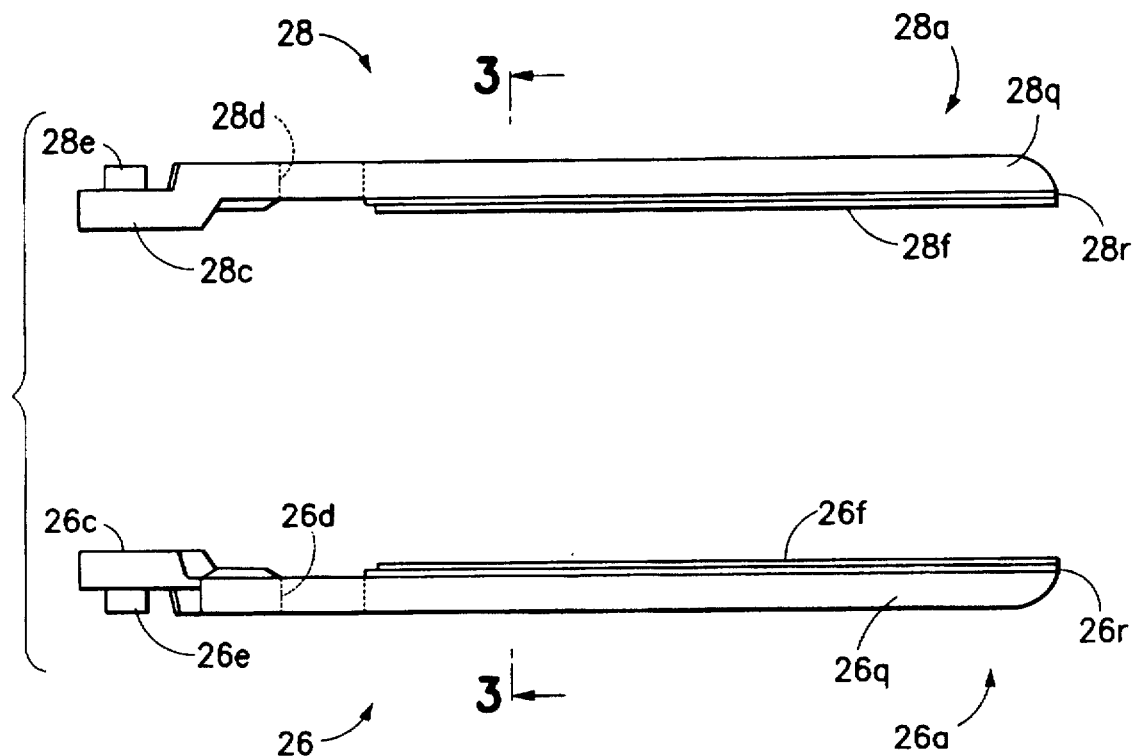
FIG. 2 is an enlarged top view of the scissor blades of FIG. 1 according to the invention.
Figure 3:
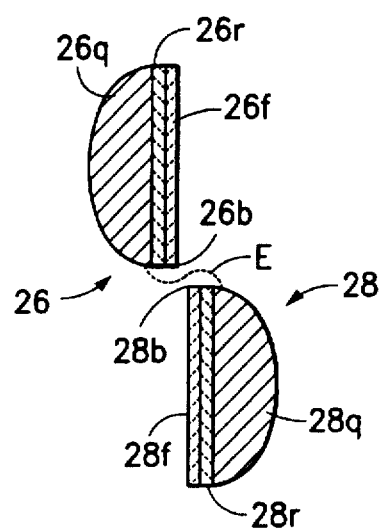
FIG. 3 is a cross sectional view of the scissor blades of FIG. 2 taken along lines 3—3 and shown in their operating positions.

Referring now to FIGS. 2 and 3, scissor blades are shown. The first scissor blade 26 has a distal portion 26a, a lower proximal tang 26c, and a mounting hole 26d therebetween. A connecting lug 26e extends orthogonally outward from the surface of the tang 26c in a first direction. The distal portion 26a includes an lower cutting edge 26b and an inner surface 26f (also called the shearing surface). Behind the inner surface 26f of the first scissor blade is an insulating layer 26r and a conducting electrode layer 26q. The opposed second scissor blade 28 is configured similarly to the first scissor blade and has a distal portion 28a, an upper proximal tang 28c, and a mounting hole 28d therebetween. A connecting lug 28e extends orthogonally from the surface of the tang 28c in a second direction which is opposite to the first direction mentioned above. The distal portion 28a includes an upper cutting edge 28b and an inner surface 28f. Behind the inner surface 28f of the second scissor blade 28 is an insulating layer 28r and a conducting electrode layer 28q.

The scissor blade assemblies 26 and 28 are laminated assemblies which include a metal support (also called a metal blade support or an outer conductive layer) 26q, 28q, an intermediate electrically insulative layer 26r, 28r and a coated face 26f, 28f defining a shearing surface. The metal support is textured according to the method of the invention, as described in detail below, and then coated with the insulative layer 26r, 28r and the face 26f, 28f. It will be appreciated that the Figures herein are not intended to depict the relative thickness of the layers according to any scale and that the thickness of the layers may be exaggerated for illustration purposes. It will be appreciated, however, that the faces 26f, 28f are preferably provided with sharpened opposed cutting edges 26b, 28b which may be achieved by sharpening either the insulating layer 26r, 28r, the blade support 26q, 28q, or both either before or after applying the face coating of titanium dioxide.

The metal blade supports 26q, 28q form the electrically conductive portions (i.e., the electrodes) of the scissor blades through which cautery current is applied. In this regard, substantially the entire lengths of blade supports 26q, 28q are conductive, including the proximal lugs 26e which make electrical connection with the respective rods 32, 34 via links 99 as described above with reference to FIG. 1. As seen in FIG. 3, the preferential path of current flow "E" is through the metal support portions 26q, 28q of the scissor blades which are insulated from the cutting edges 26b, 28b and the shearing surfaces (faces) 26f, 28f of the blades. Because of this arrangement, cautery and coagulation current may be applied continuously throughout the cutting/shearing procedure since the contact of the cutting edges and shearing surfaces of the blades will not short circuit the device. The titanium dioxide coating on the ceramic insulative layer gives the blades the operational feel of having metal on metal shearing surfaces. Additional embodiments of scissor blades are found in co-pending application U.S. Ser. No. 08/429,596 which has been incorporated herein by reference.

According to the method of the invention, an investment mold having a textured interior cavity is made for forming at least one blade, and preferably numerous blades for endoscopic bipolar scissors instruments. Preferably, the texture of the cavity is caused to be at least as irregular as that of gritblasted blades.

In order to create an investment mold having a textured interior cavity, a (typically metal) injection mold for one or more endoscopic scissor blade patterns is made. The injection mold cavity is then textured in desired areas according to any of several methods. In a first method of texturing the interior cavity of the injection mold, the cavity of the mold is chemically etched. In a second embodiment, the cavity of the injection mold is textured by abrasive (grit) blasting. In a third embodiment, the cavity of the mold is textured via electro-discharge machining (EDM); i.e., by varying the current density of the EDM, the wire of the EDM will create the desired roughness of texture.

Using any of the methods for texturing the injection mold, the wax blade patterns molded therefrom will have the requisite roughness so that when an investment mold is made from these patterns, the investment mold, and hence the metal blades cast in it will also have the necessary roughness; i.e., the blades will be sufficiently rough so that they may be coated with ceramic without the necessity of first gritblasting the blades.

After the investment mold for the blades has been appropriately textured, the blades are cast in a manner well known in the art. Preferably the blades are made of stainless steel or superalloy, although any suitably strong conductive material may be used. Subsequently the blades are coated along the cutting and/or shearing surface with one or more layers of insulators and/or lubricous materials, as desired, using a plasma thermal spray or similar technique, in a manner also known in the art. Preferably the insulator is alumina ($Al_2O_3$), although any suitable ceramic may be used. If a metal-on-metal operational feel to the blades is desired, the coated face is preferably a titanium dioxide ceramic ($TiO_2$), although zirconium dioxide ($ZiO_2$) or chromium dioxide ($CrO_2$) ceramics can be used. The resulting blades are used in the assembly of an endoscopic bipolar scissors instrument.

There have been described and illustrated herein several embodiments of texturing endoscopic surgical scissor blades. While particular embodiments of the invention have been described, it is not intended that the invention be limited thereto, as it is intended that the invention be as broad in scope as the art will allow and that the specification be read likewise. Thus, while a particular texture for the cavity of the mold (that of being at least as irregular as gritblasted blades) has been disclosed, it will be appreciated that other levels of texturing more or less irregular than that of gritblasted blades can be used as well. Also while particular bipolar surgical instrument incorporating the textured scissor blades has been described, it will be appreciated by those skilled in the art that other surgical instruments, whether non-cautery, monopolar or bipolar, and using other actuating mechanisms can be provided. Furthermore, while particular methods for roughening the cavity of the injection mold were described, it will be appreciated that other methods could be utilized. It will therefore be appreciated by those skilled in the art that yet other modifications could be made to the provided invention without deviating from its spirit and scope as so claimed.

We claim:

1. A method of manufacturing an endoscopic scissor blade, comprising:
   a) obtaining an investment mold with a textured interior cavity surface for casting an endoscopic scissors blade;
   b) forming the endoscopic scissors blade with a textured outer surface by casting metal material in the investment mold; and
   c) coating the textured outer surface of the scissors blades with a ceramic material.

2. A method according to claim 1, wherein:
   said textured interior cavity surface has a roughness approximately at least as rough as a roughness of gritblasted scissors blade.

3. A method according to claim 1, wherein:
   said ceramic material comprises alumina.

4. A method according to claim 1, wherein:
   said ceramic material comprises at least one of titanium dioxide, zirconium dioxide, and chromium dioxide.

5. A method according to claim 1, wherein:
   said textured interior cavity surface of said investment mold is textured only where the scissors blade formed therein will be coated with said ceramic material.

6. A method according to claim 1, wherein:
   said obtaining an investment mold with a textured interior cavity comprises forming an injection mold having an interior cavity surface, texturing said interior cavity surface, forming a blade pattern in the injection mold, said blade pattern having a textured surface, and using said blade pattern having a textured surface to obtain said investment mold with a textured interior cavity.

7. A method according to claim 6, wherein:

said texturing said interior cavity surface comprises etching said interior cavity surface.

8. A method according to claim 6, wherein:

said texturing said interior cavity surface comprises grit-blasting said interior cavity surface.

9. A method according to claim 6, wherein:

said texturing said interior cavity surface comprises electro-discharge machining said interior cavity surface.

10. An endoscopic scissors blade, comprising:

a metal blade member having a textured outer surface formed by the process of casting a metal material into an investment mold which is provided with a textured interior cavity surface, and a ceramic layer coated on said textured outer surface of said blade member.

11. An endoscopic scissors blade according to claim 10, wherein:

said ceramic layer comprises alumina.

12. An endoscopic scissors blade according to claim 10, wherein:

said ceramic layer comprises at least one of titanium dioxide, zirconium dioxide, and chromium dioxide.

13. An endoscopic scissors blade according to claim 10, wherein:

said metal material is stainless steel.

14. A bipolar electrosurgical instrument for cutting and coagulating tissue, comprising:

a) first and second metal blade members formed by the process of casting metal material into an investment mold which is provided with a textured interior cavity surface, and by coating a ceramic material on a textured outer surface of the so formed metal blade members;

b) means for pivotally joining said first and second blade members together;

c) means coupled to at least one of said first and second blade members for imparting a scissors-like movement between said first and second blade members; and d) means for applying a voltage to at least one of said first and second metal blade members.

15. A bipolar electrosurgical instrument according to claim 14, wherein:

said first and second metal blade members are endoscopic first and second metal blade members, and said means for imparting a scissors-like movement comprises at least one conducting rod coupled to said first and second blade members, a tube coupled to said means for pivotally joining, and a handle means for moving said at least one conducting rod relative to said tube.

16. A bipolar electrosurgical instrument according to claim 14, wherein:

said ceramic material is substantially non-conductive.

* * * * *